United States Patent [19]

Andersen et al.

[11] Patent Number: 5,348,965
[45] Date of Patent: Sep. 20, 1994

[54] N-SUBSTITUTED AZAHETEROCYCLIC CARBOXYLIC ACIDS

[75] Inventors: Knud E. Andersen, Smorum; Lars J. S. Knutsen, Vedbaek; Per O. Sorensen, Frederiksberg; Behrend F. Lundt, Kokkedal; Jesper Lau, Farum; Hans Petersen, Vanlose, all of Denmark

[73] Assignee: Novo Nordisk A/S, Bagsvaerd, Denmark

[21] Appl. No.: 882,788

[22] Filed: May 14, 1992

[30] Foreign Application Priority Data

May 17, 1991 [DE] Fed. Rep. of Germany ....... 0937/91

[51] Int. Cl.$^5$ ................. C07D 211/14; C07D 211/70; A61K 31/445
[52] U.S. Cl. .................................. 514/325; 546/203; 546/204
[58] Field of Search ................. 546/203, 204; 514/325

[56] References Cited

U.S. PATENT DOCUMENTS 3,177,211  4/1965  Zenitz et al. ................ 260/243

FOREIGN PATENT DOCUMENTS

| 0221572 | 5/1987 | European Pat. Off. ............ 546/203 |
| 0342635 | 11/1989 | European Pat. Off. ............ 546/193 |
| 0346927 | 12/1989 | European Pat. Off. ............ 546/203 |
| 0374801 | 6/1990 | European Pat. Off. ............ 546/208 |
| 830709 | 3/1960 | United Kingdom ................ 544/38 |
| 905692 | 9/1962 | United Kingdom ................ 544/39 |

*Primary Examiner*—C. Warren Ivy
*Assistant Examiner*—Phyllis G. Spivak
*Attorney, Agent, or Firm*—Steve Zelson; Elias Lambiris

[57] ABSTRACT

The invention relates to therapeutically active azaheterocyclic compounds and to pharmaceutical compositions comprising the compounds. The novel compounds are useful in treating a central nervous system ailment related to the GABA uptake.

16 Claims, No Drawings

N-SUBSTITUTED AZAHETEROCYCLIC CARBOXYLIC ACIDS

FIELD OF THE INVENTION

The present invention relates to novel N-substituted azaheterocyclic carboxylic acids and esters thereof in which a substituted alkyl chain forms part of the N-substituent and salts thereof, to methods for their preparation, to compositions containing them, and to their use for the clinical treatment of abnormal function of the γ-aminobutyric acid neurotransmission system.

BACKGROUND OF THE INVENTION

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA' ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68-112).

A well-known and potent inhibitor of GABA uptake from the synaptic cleft into presynaptic nerve terminals and glial cells is, for example, 3-piperidinecarboxylic acid (nipecotic acid). However, being a relatively polar compound and therefore unable to cross the blood-brain barrier, 3-piperidinecarboxylic acid itself has found no practical utility as a drug.

In U.S. Pat. No. 4,383,999 and No. 4,514,414 (SmithKline Beckman Corporation) and in EP 236342 as well as in EP 231996 (Novo Industri A/S) some derivatives of N-(4,4-disubstituted-3-butenyl)azaheterocyclic carboxylic acids are claimed as inhibitors of GABA uptake. In EP 342635 and EP 374801 (Novo Industri A/S), N-substituted azaheterocyclic carboxylic acids in which an oxime ether group and vinyl ether group forms part of the N-substituent respectively are claimed as inhibitors of GABA uptake. EP 221572 (Warner-Lambert Company) claims that 1-aryloxyalkylpyridine-3-carboxylic acids are inhibitors of GABA uptake.

In addition to the above cited references, U.S. Pat. No. 2,976,286 and British Patent No. 905,692 discloses 10-(dialkylaminoethoxyethyl)phenothiazines and U.S. Pat. No. 2,965,639 discloses 5-(dialkylaminoethoxyethyl)-10,11-dihydrodibenzo[b,f]azepines. The compounds of U.S. Pat. No. 2,965,639 and British patent No. 905,692 are disclosed for having antihistaminic, spasmolytic, anti-inflammatory, sedative and ganglion-blocking activity. The compounds of the present invention essentially differ from the compounds in U.S. Pat. No. 2,976,286, U.S. Pat. No. 2,965,639 and British Patent No. 905,692 by the amino acid moiety important for the inhibition of GABA uptake.

According to Yunger, L. M. et al., J. Pharm. Exp. Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl)nipecotic acid (designated SK&F 100604J) are orally active inhibitors of GABA uptake. These data are summarized in Krogsgaard-Larsen, P. et al., Epilepsy Res. 1987, 1, 77-93.

Guvacine is 1,2,5,6-tetrahydropyridine-3-carboxylic acid and homo-β-proline is pyrrolidine-3-acetic acid.

DESCRIPTION OF THE INVENTION

The present invention relates to novel N-substituted azaheterocyclic carboxylic acids and esters thereof of formula I

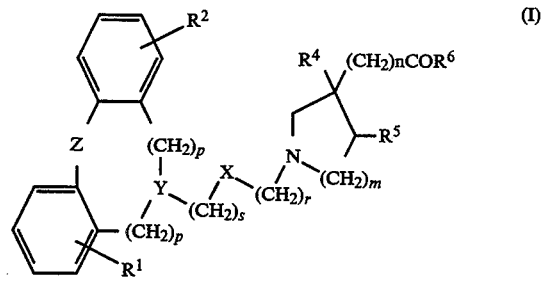

wherein
$R^1$ and $R^2$ are hydrogen, halogen, trifluoromethyl, $C_{1-6}$-alkyl or $C_{1-6}$-alkoxy;
Y is $>N-CH_2-$, $>CH-CH_2-$ or $>C=CH-$ when s is 0, 1 or 2 or Y is $>\underline{CH}-CH=N-$ or $>\underline{C}=N-$ when s is 0 wherein the underscored atom participates in the ring system;
X is $-O-$;
Z is $-O-$, $-S-$, $-CH_2-$, $-CH_2CH_2-$, $-CH=CH-CH_2-$, $-CH_2-CH=CH-$, $-CH_2CH_2CH_2-$, $-CH=CH-$ or $-O-CH_2-$;
$R^4$ and $R^5$ each represents hydrogen or may when m is 2 together represent a bond;
$R^6$ is OH or $C_{1-8}$-alkoxy;
p is 0 or 1;
q is 0 or 1;
s is 0, 1 or 2;
r is 2, 3 or 4;
m is 1 or 2;
n is 1 when m is 1 or n is 0 when m is 2; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts or- when the carboxylic acid group is not esterified—as pharmaceutically acceptable metal salts or—optionally alkylated—ammonium salts.

Pharmaceutically acceptable acid addition salts of compounds of formula 1 include those derived from inorganic or organic acids such as hydrochloric, hydrobromic, sulfuric, acetic, phosphoric, lactic, maleic, phthalic, citric and fumaric acid.

The compounds of formula I have a greater lipophilicity—and thus a greater availability to the brain—as well as a far higher affinity to the GABA uptake sites than the parent compounds without the N-substituent (i.e. nipecotic acid, guvacine and homo-β-proline).

It has been demonstrated that the novel compounds of formula I which inhibit the uptake of GABA from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The compounds of formula I are prepared by the following methods:

Method A:

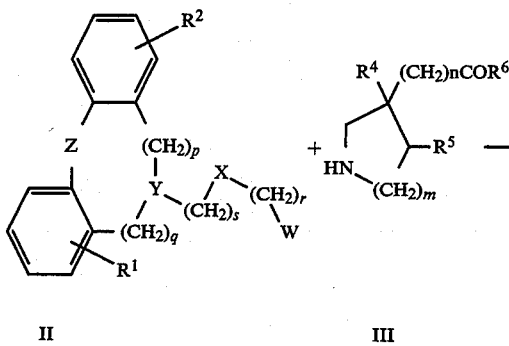

A compound of formula II wherein $R^1$, $R^2$, X, Y, Z, p, q, r and s are as defined above and W is a suitable leaving group such as halogen, p-toluene sulphonate or mesylate, is allowed to react with an azaheterocyclic compound of formula III wherein $R^4$, $R^5$, $R^6$, m and n are as defined above. This alkylation reaction may be carried out in a solvent such as acetone, dibutylether, 2-butanone, tetrahydrofuran or toluene in the presence of a base e.g. potassium carbonate and a catalyst, e.g. an alkali metal iodide at a temperature up to reflux temperature for the solvent used for e.g. 1 to 120 h. If esters have been prepared in which $R^6$ is alkoxy, compounds of formula I wherein $R^6$ is alkoxy, compounds of formula I wherein $R^6$ is OH are prepared by hydrolysis of the ester group, preferably at room temperature in a mixture of an aqueous alkali metal hydroxide solution and an alcohol such as methanol or ethanol for about 0.5 to 6 h.

Compounds of formula I, in which $R^4$ and $R^5$ does not represent a bond; Z does not represent —S—, —CH=CH—, —CH=CH—CH$_2$— or CH$_2$—CH=CH—; and Y represents >$\underline{C}$H—CH$_2$—, are prepared by method B:

Method B:

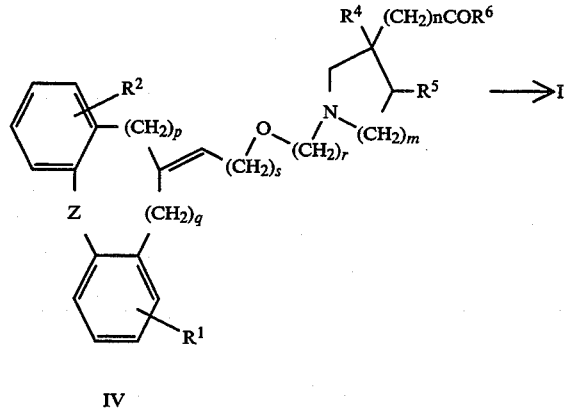

A compound of formula IV wherein $R^1$, $R^2$, $R^4$, $R^5$, $R^6$, r, s, p, q, m, n and Z are as defined above, except that $R^4$ and $R^5$ must not represent a bond and Z must not be —S—, —CH=CH—, —CH=CH—CH$_2$— or —CH$_2$—CH=CH—, is hydrogenated to give I. This reduction is carried out in a solvent such as methanol in the presence of a catalyst e.g. palladium on carbon at a pressure of e.g. 1 to 10 atm. and reaction time about 0.5 to 18 h.

If esters have been prepared in which $R^6$ is alkoxy, compounds of formula I wherein $R^6$ is OH are prepared by hydrolysis of the ester group, preferably at room temperature in a mixture of an aqueous alkali metal hydroxide solution and an alcohol such as methanol or ethanol for about 0.5 to 6 h.

Compounds of formula II and III are prepared by methods familiar to those skilled in the art.

Under certain circumstances it is necessary to protect the intermediates used in the above methods e.g. a compound of formula III with suitable protecting groups. The carboxylic acid group can for example be esterified. Introduction and removal of such groups is described in "Protective Groups in Organic Chemistry" J. F. W. McOrnie ed. (New York, 1973).

PHARMACOLOGICAL METHODS

Values for in vitro inhibition of [$^3$H]-GABA uptake for the invention compounds were assessed essentially by the method of Fjalland (Acta Pharmacol. Toxicol. 1978, 42, 73–76).

Male wistar rat cortical tissue was gently homogenized by hand using a glass/PTFE homogenizer in 10 volumes of 0.32 M sucrose. Incubation was performed in a 40 mM tris HCl buffer (pH 7.5 at 30° C.) containing 120 nM NaCl, 9.2 nM KCl, 4 mM MgSO$_4$, 2.3 nM CaCl$_2$ and 10 mM glucose, for 60 minutes at 30° C.

Values for inhibition of GABA uptake for some representative compounds are recorded in Table I.

TABLE I

| Inhibition of [$^3$H]-GABA uptake | |
|---|---|
| Example no. | IC$_{50}$ (nM) in vitro |
| 1 | 222 |
| 2a | 306 |
| 2c | 119 |
| 3 | 754 |
| 5 | 900 |
| 7 | 1128 |
| 10 | 617 |
| 11 | 162 |
| 12 | 724 |
| 17 | 66 |
| 18 | 1326 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or nonaqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The route of administration may be any route, which effectively transports the active compound to the appropriate or desired site of action, such as oral or parenteral, the oral route being preferred.

EXAMPLES

The process for preparing compounds of formula I is further illustrated in the following examples which however are not to be construed as limiting.

Hereinafter, TLC is thin layer chromatography and THF is tetrahydrofuran, CDCl₃ is deuterio chloroform and DMSO-d₆ is hexadeuterio dimethylsulfoxide. The structures of the compounds are confirmed by either elemental analysis or NMR, where peaks assigned to characteristic protons in the title compounds are presented where appropriate. NMR shifts (δ) are given in parts per million (ppm). M.P. is melting point and is given in °C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

EXAMPLE (R)-N-(2-(2-(10,11-Dihydro-5H-dibenz[b,f]azepin-5-yl)ethoxy)ethyl)-3-piperidinecarboxylic acid hydrochloride A mixture of sodium hydride (0.40 g, 0.010 mol, 60% oil dispersion) and 10,11-dihydro-5H-dibenz[b,f]azepine (1.95 g, 0.010 mol) in dry dibutylether (30 ml) was heated at reflux temperature for 3.5 h under an atmosphere of nitrogen. The reaction mixture was cooled to 100° C. and bis-2-chloro-ethyl ether (4.7 ml) was added and the mixture was heated at reflux temperature for 16 h. The reaction mixture was cooled and water (50 ml) was added. The mixture was extracted with toluene (100 ml). The organic extract was dried over sodium sulphate and the solvent evaporated in vacuo to give 2.8 g of an oily residue containing 2-chloro-1-(2-(10,11-dihydro-5H-dibenz[b,f]-azepin-5-yl)ethoxy)ethane. To this oil was added ethyl (R)-3-piperidinecarboxylate (3.0 g, 0.019 mol) and the mixture was heated at 150° C. for 1.5 h. The reaction mixture was allowed to cool to 80° C. and toluene (100 ml) was added. The mixture was then allowed to cool to room temperature and a solution of potassium carbonate (1.4 g) in water (100 ml) was added. The phases were separated and the organic phase was washed successively with water, an aqueous sodium acetate solution (pH 5) and an aqueous citric acid solution (pH 5). The organic phase was then extracted with a 5% aqueous citric acid solution (50 ml). The acidic (pH 1) aqueous extract was washed with toluene (2×50 ml) and then a 4 N sodium hydroxide solution was added until pH 6–7. The aqueous mixture was extracted with toluene and the organic extract was treated with charcoal and dried over sodium sulphate. The solvent was evaporated in vacuo to give 2.1 g (50%) of (R)-N-(2-(2-(10,11-dihydro-5H-dibenz[b,f]azepin-5-yl)ethoxy)ethyl)-3-piperidinecarboxylic acid ethyl ester as an oil. TLC: rf=0.20 (SiO₂; n-heptane/THF=7:3).

The above ester was dissolved in ethanol (10 ml) and a 12 N sodium hydroxide solution (1.25 ml) was added. The mixture was stirred at room temperature for 4 h. A concentrated hydrochloric acid solution was added until pH 1. Dichloromethane (300 ml) was added followed by water until the solid material was dissolved. The phases were separated and the organic phase was dried over sodium sulphate. The solvent was evaporated in vacuo to give a residue, which was re-evaporated twice with acetone and then recrystallized from a mixture of acetone and ethyl acetate. This afforded 1.4 g (65%) of the title compound.

M.P. 147°–149°. Calculated for $C_{24}H_{31}ClN_2O_3 \cdot \frac{1}{4} H_2O$: C, 66.2%; H, 7.3%; Cl, 8.1%; N, 6.4%; Found: C, 66.2%; H, 7.4%; Cl, 8.1%; N, 6.3%.

EXAMPLE 2a (R)-N-(2-(2-(10H-Phenothiazin-10-yl)ethoxy)ethyl)-3-piperidinecarboxylic acid hydrochloride Phenothiazine (3.8 g, 19 mmol) was added to a suspension of sodium hydride (0.92 g, 23 mmol, 60% oil dispersion) in dry dibutylether (25 ml) under an atmosphere of nitrogen. The mixture was heated at 135° C. for 1 h and then cooled to approximately 100° C. 2-(2-

((tetrahydro-2-pyranyl)oxy)ethoxy)ethylchloride (8 g, 38 mmol) was added in one portion and the mixture was heated overnight at 110° C. The reaction mixture was poured into water (250 ml) and extracted with dichloromethane (3×50 ml) and diethyl ether (50 ml). The combined organic extracts were washed with brine and dried over sodium sulphate. The solvent was evaporated in vacuo leaving an oil, which was submitted to column chromatography using dichloromethane as eluent. Collecting the proper fractions afforded 3.9 g of crude 10-(2-(2-((tetrahydro-2-pyranyl)oxy)ethoxy)ethyl)-10H-phenothiazine. TLC: rf=0.72 (SiO$_2$; dichloromethane/methanol=19:1).

A mixture of crude 10-(2-(2-((tetrahydro-2-pyranyl)oxy)ethoxy)ethyl)-10H-phenothiazine (3.8 g, 10 mmol), 2-propanol (50 ml) and a 4 M aqueous sulfuric acid solution (8 ml) was heated at 60° C. for 3 h and then left overnight at room temperature. The reaction mixture was poured into a mixture of water (500 ml) and a 4 N sodium hydroxide solution (17 ml). The mixture was extracted with diethyl ether (150 ml) and the organic extract was washed with brine and dried over sodium sulphate. The solvent was evaporated in vacuo to give 1.5 g of crude 2-(2-(10H-phenothiazin-10-yl)ethoxy)ethanol. TLC: rf=0.52 (SiO$_2$; dichloromethane/methanol=19:1).

A well-stirred mixture of the above alcohol (1.5 g, 5.2 mmol), triethylamine (1.8 ml) and toluene (20 ml) placed under an atmosphere of nitrogen was cooled on an ice-bath. A solution of methanesulfonyl chloride (1.5 g, 10.4 mmol) in toluene (5 ml) was added within 15 minutes. Stirring was continued for 45 minutes on an ice-bath and then for 30 minutes at room temperature. Water (15 ml) was added and the mixture was stirred at room temperature for 15 minutes. The phases were separated and the aqueous phase was extracted with toluene (20 ml). The combined organic extracts were washed with a 5% sodium bicarbonate solution, brine and then dried over sodium sulphate. The solvent was evaporated in vacuo to give an oil, which was dissolved in toluene (30 ml). To this solution was added potassium carbonate (2.5 g, 18.3 mmol) and ethyl (R)-3-piperidinecarboxylate tartrate (3.2 g, 10.4 mmol) and the suspension was heated at reflux temperature for 3 days. The cooled reaction mixture was filtered and the solid washed with a small portion of toluene. The solvent was evaporated from the filtrate in vacuo to give a residue, which was dissolved in a mixture of ethyl acetate (30 ml) and water (30 ml). A 34% aqueous solution of tartaric acid was added until pH 4. The phases were separated and the aqueous phase was extracted with ethyl acetate (15 ml). To the combined organic phases were added water (10 ml) and a 34% aqueous solution of tartaric acid (3.5 ml). The phases were separated and the organic phase was extracted with a mixture of water (10 ml) and a 34% aqueous solution of tartaric acid (2 ml). The acidic aqueous phases are combined and washed with ethyl acetate (15 ml). All the organic phases were discarded and to the acidic aqueous phase was added ethyl acetate (50 ml) and water (50 ml). A 4 N sodium hydroxide solution was added until pH 8.5 and the phases were separated. The aqueous phase was extracted with ethyl acetate (15 ml) and the combined organic phases were washed with brine and dried over sodium sulphate. The solvent was evaporated in vacuo to give 0.8 g of (R)-N-(2-(2-(10H-phenothiazin-10-yl)ethoxy)ethyl)-3-piperidinecarboxylic acid ethyl ester as an oil. TLC: rf=0.20 (SiO$_2$; dichloromethane/methanol/acetic acid=20:2:1 ).

The above ester (0.8 g, 1.8 mmol) was dissolved in ethanol (15 ml) and a 4 N sodium hydroxide solution (2 ml) was added. The mixture was stirred vigorously at room temperature for 4 h. The solvent was evaporated in vacuo to give an oily residue. Dichloromethane (100 ml) was added and the mixture was cooled on an ice-bath. A concentrated hydrochloric acid solution (1 ml) was added. The mixture was stirred vigorously for a few minutes and the phases were separated. The organic phase was dried over sodium sulphate and the solvent was evaporated in vacuo. The residue was re-evaporated with dichloromethane, dissolved in dichloromethane and left overnight at 4° C. The solid formed was isolated by filtration to give 0.6 g of the title compound as a solid.

M.P. 188°–189° C. Calculated for C$_{22}$H$_{27}$ClN$_2$O$_3$S: C, 60.7%; H, 6.3%; N, 6.4%; Found: C, 60.4%, H, 6.3%; N, 6.3%.

The following compounds were prepared by a similar procedure:

EXAMPLE 2b (R)-N-(2-(2-(10H-Phenoxazin-10-yl)ethoxy)ethyl)-3-piperidinecarboxylic acid hydrochloride After an alkaline hydrolysis similar to that described above, the dichloromethane extract was dried over sodium sulphate and evaporated in vacuo. The foamy residue was heated to reflux temperature with acetone, cooled, filtered and dried to give 1.7 g of the title compound as a solid.

M.P. 161°–164° C. Calculated for C$_{22}$H$_{28}$ClN$_2$O$_4$: C, 63.1%; H, 6.5%; N, 6.7%; Found: C, 63.1%; H, 6.6%; N, 6.4%.

EXAMPLE 2c (R)-N-(2-(2-(2-Chloro-10H-phenothiazin-10-yl)ethoxy)ethyl)-3-piperidinecarboxylic acid hydrochloride After an alkaline hydrolysis similar to that described above, the dichloromethane extract was dried over magnesium sulphate and evaporated in vacuo. The foamy residue was heated in acetone, cooled, filtered and dried to give 2.3 g of the title compound as an amorphous solid.

M.P. 75° C. Calculated for C$_{22}$H$_{25}$ClN$_2$O$_3$S.HCl.H$_2$O: C, 54.2%; H, 5.8%; N, 5.8%; Found: C, 54.8%; H, 5.7%; N, 5.5%.

EXAMPLE 2d (S)-N-(2-(2-(2-(Trifluoromethyl)-10H-phenothiazin-10-yl)ethoxy)ethyl)-3-piperidinecarboxyl acid hydrochloride After an alkaline hydrolysis similar to that described above, the dichloromethane extract was dried over magnesium sulphate and evaporated in vacuo. The residue was re-evaporated twice with acetone and dissolved in acetone (20 ml) and left for crystallization. The solid formed was isolated by filtration and dried to give 1.9 g of the title compound as an amorphous solid.

M.P. 115° C. Calculated for C$_{23}$H$_{26}$ClF$_3$N$_2$O$_3$S: C, 54.9%; H, 5.2%; N, 5.6%; Found: C, 54.7%; H, 5.4%; N, 5.4%.

$^1$H NMR (DMSO-d$_6$) δ4.20 (t, 2H).

EXAMPLE 3

(R)-N-(2-(2-(10,11-Dihydro-5H-dibenzo[a,d]cyclohepten-5-ylidene)ethoxy)ethyl)-3-piperidinecarboxylic acid hydrochloride A solution of 10,11-dihydro-5H-dibenzo[a,d]cyclohepten-5-one (9.4 g, 0.045 mol) in dry THF (100 ml) was placed under an atmosphere of nitrogen. A solution of vinylmagnesium bromide in THF (100 ml, 0.5 M) was added in such a rate to keep the reaction temperature at 30°-35° C. When addition was complete the mixture was heated at 50°-60° C. for 1.5 h. The reaction mixture was cooled on an ice-bath and a solution of ammonium chloride (10 g) in water (50 ml) was carefully added. Diethyl ether (100 ml) was added and the phases were separated. The aqueous phase was extracted with diethyl ether (100 ml) and the combined organic phases were dried over sodium sulphate. The solvent was evaporated in vacuo to give a residue which was re-evaporated twice with dichloromethane to give 11.8 g of crude 5-ethenyl-10,11-dihydro-5H-dibenzo[a,d]cyclohepten-5-ol.

The above crude alcohol (9.2 g) was dissolved in dichloromethane (100 ml) and the mixture was placed on an ice-bath. A solution of trimethylsilyl bromide (6.6 g, 0.043 mol) in dichloromethane (50 ml) was added dropwise within 30 minutes. When addition was complete the mixture was stirred at room temperature for 45 minutes. Icewater (50 ml) and a saturated aqueous sodium bicarbonate solution (200 ml) was added. The phases were separated and the organic phase was dried over sodium sulphate. The solvent was evaporated in vacuo to give a residue, which was re-evaporated with cyclohexane. This afforded 10.5 g of crude 5-(2-bromoethylidene)-10,11-dihydro-5H-dibenzo[a,d]cycloheptene.

A solution of n-butyllithium in hexanes (12 ml, 2.5 M) was added dropwise to ice-cooled ethylene glycol (25 ml) under an atmosphere of nitrogen. When addition was complete the mixture was stirred at room temperature for 30 minutes. A solution of the above crude bromide (7.1 g) in cyclohexane (20 ml) was added in one portion and the hexanes were removed by vigorous stirring and a strong nitrogen flow. Then the reaction mixture was stirred at room temperature for 68 h. Water (30 ml) was added and the mixture was extracted with ethyl acetate (3×50 ml). The combined organic extracts were dried over sodium sulphate and the solvent was evaporated in vacuo. The oily residue was submitted to column chromatography on silica gel (150 g) using a mixture of THF and n-heptane (3:7) as eluent. Collecting the proper fractions afforded 2.4 g of 5-(2-(2-hydroxyethoxy)ethylidene)-10,11-dihydro-5H-dibenzo[a,d]cycloheptene as an oil. TLC: rf=0.18 (SiO$_2$; THF/n-heptane=3:7).

A solution of the above alcohol (3.7 g, 13.2 mmol)) in dry THF (40 ml) was placed under an atmosphere of nitrogen and placed on an ice-bath. A solution of n-butyllithium in hexanes (3.7 ml, 2.5 M) was added dropwise and the mixture was stirred for another 15 minutes. p-Toluenesulfonyl chloride (2.5 g, 13.2 mmol) was added in one portion and the mixture was stirred on an ice-bath for 1 h. The solvent was evaporated in vacuo keeping the bath temperature below 20° C. The residue was dissolved in acetone (25 ml) and ethyl (R)-3-piperidinecarboxylate (3.1 g, 19.8 mmol) and potassium carbonate (3.3 g, 24.0 mmol) were added. The mixture was stirred at room temperature for 140 h. The mixture was filtered and the solvent was evaporated in vacuo. The oily residue was submitted to column chromatography on silica gel (200 g) using a mixture of ethyl acetate and n-heptane (1:1) as eluent. Collecting the proper fractions afforded 1.7 g of (R)-N-(2-(2-(10,11-dihydro-5H-dibenzo[a,d]cyclohepten-5-ylidene)ethoxy)ethyl)-3-piperidinecarboxylic acid ethyl ester as an oil. TLC: rf=0.19 (SiO$_2$; ethyl acetate/n-heptane=1:1 ).

The above ester (1.7 g, 4.1 mmol) was dissolved in ethanol (15 ml) and a 4 N sodium hydroxide solution (3.5 ml) was added. The mixture was stirred vigorously at room temperature for 5 h. Dichloromethane (300 ml) was added followed by a 4 N hydrochloric acid solution until pH 1. The mixture was stirred vigorously for a few minutes and the phases were separated. The organic phase was dried over sodium sulphate and the solvent was evaporated in vacuo. The residue was re-evaporated twice with acetone, once with ethyl acetate and once with diethyl ether to give 1.7 g of the title compound as a solid which was recrystallized from acetone.

M.P. 157°-159° C. Calculated for C$_{25}$H$_{30}$ClNO$_3$: C, 70.2%; H, 7.1%; N, 3.3%; Found: C, 70.1%; H, 7.1%; N, 3.2%.

EXAMPLE 4

(R)-N-(2-(2-(10,11-Dihydro-5H-dibenzo[a,d]cyclohepten-5-yl)ethoxy)ethyl)-3-piperidinecarboxylic acid hydrochloride The acid prepared in Example 3 (0.2 g, 0.5 mmol) was dissolved in methanol (10 ml) and stirred under an atmosphere of hydrogen for 16 h at room temperature in the presence of 10% palladium on carbon catalyst (50% aqueous paste). The mixture was filtered and the solvent was evaporated in vacuo to give an oily residue, which was re-evaporated from acetone and then crystallized from acetone (10 ml). This afforded 0.13 g (65%) of the title compound.

M.P 147°-148° C.

$^1$H NMR (DMSO-d$_6$) δ4.24 (brs, 1H).

EXAMPLE 5

(R)-N-(3-(2-(10,11-Dihydro-5H-dibenzo[a,d]cyclohepten-5-ylidene)ethoxy)-1-propyl)-3-piperidinecarboxylic acid hydrochloride A solution of n-butyllithium in hexanes (16.8 ml, 2.5 M) was added dropwise to ice-cooled propylene glycol (25 ml) under an atmosphere of nitrogen. When addition was complete the mixture was stirred at room temperature for 15 minutes. A solution of crude 5-(2-bromoethylidene)-10,11-dihydro-5H-dibenzo[a,d]cycloheptene (10.1 g, prepared as described in Example 3) was added in one portion and the reaction mixture was stirred at room temperature for 42 h. Water (40 ml) was added and the mixture was extracted with ethyl acetate (3×75 ml). The combined organic extracts were washed with water (15 ml), dried over sodium sulphate and the solvent was evaporated in vacuo. The oily residue was submitted to column chromatography on silica gel (200 g) using a mixture of THF and n-heptane (3:7) as eluent. Collecting the proper fractions afforded 4.2 g of 5-(2-(3-hydroxypropyloxy)ethylidene)-10,11-dihydro-5H-dibenzo[a,d]cycloheptene as an oil. TLC: rf=0.18 (SiO$_2$; THF/n-heptane=3:7).

A solution of the above alcohol (4.2 g, 14.3 mmol) in dry THF (30 ml) was placed under an atmosphere of nitrogen and placed on an ice-bath. A solution of n-butyllithium in hexanes (5.7 ml, 2.5 M) was added dropwise within 15 minutes and the mixture was stirred for another 15 minutes. p-Toluenesulfonyl chloride (2.7 g, 14.0 mmol) was added in one portion and the mixture was stirred at room temperature for 30 minutes. The solvent was evaporated in vacuo keeping a low bath temperature. The oily residue was dissolved in acetone (25 ml) and ethyl (R)-3-piperidinecarboxylate (3.3 g, 21.0 mmol) and potassium carbonate (3.5 g, 25.0 mmol) were added. The mixture was stirred at room temperature for 120 h. The mixture was filtered and the solvent was evaporated in vacuo. The oily residue was submitted to column chromatography on silica gel (100 g) using a mixture of ethyl acetate and n-heptane (2:3) as eluent. Collecting the proper fractions afforded 3.0 g of (R)-N-(3-(2-(10,11-dihydro-5H-dibenzo[a,d]cyclohepten-5-ylidene)ethoxy)-1-propyl)-3-piperidinecarboxylic acid ethyl ester as an oil. TLC: rf=0.19 ($SiC_2$; ethyl acetate/n-heptane=1:1).

The above ester (2.5 g, 5.8 mmol) was dissolved in ethanol (15 ml) and a 4 N sodium hydroxide solution (4.3 ml) was added. The mixture was stirred vigorously at room temperature for 5 h. A 4 N hydrochloric acid solution was added until pH 1 followed by dichloromethane (400 ml). The mixture was stirred vigorously for a few minutes and the phases were separated. The organic phase was dried over sodium sulphate and the solvent was evaporated in vacuo. The residue was evaporated twice with acetone, once with ethyl acetate, dissolved in acetone (15 ml) and left for crystallization. This afforded 1.9 g of the title compound as a solid.

M.P. 78°–80° C. Calculated for $C_{26}H_{32}ClNO_3 \cdot \frac{3}{4}H_2O$: C, 68.6%; H, 7.4%; N, 3.1%; Cl, 7.8%; Found: C, 68.3%; H, 7.3%; N, 3.0%; Cl, 7.8%.

EXAMPLE 6

(R)-N-(3-(2-(10,11-Dihydro-5H-dibenzo[a,d]cyclohepten-5-yl)ethoxy)-1-propyl)-3-piperidinecarboxylic acid hydrochloride The acid prepared in Example 5 (0.5 g, 1.1 mmol) was dissolved in methanol (15 ml) and stirred under an atmosphere of hydrogen for 8 h at room temperature in the presence of 10% palladium on carbon catalyst (50% aqueous paste). The mixture was filtered and the solvent was evaporated in vacuo to give an oily residue which was re-evaporated from acetone and then crystallised from a mixture of acetone and ethyl acetate. This afforded 0.3 g (60%) of the title compound as an amorphous solid.

M.P. 80°–81° C.
$^1$H NMR (DMSO-$d_6$) δ4.21 (brs, 1H).

EXAMPLE 7

(R)-N-(2-(((10,11-Dihydro-5H-dibenzo[a,d]cyclohepten-5-ylidene)amino)oxy)ethyl)-3-piperidinecarboxylic acid hydrochloride A mixture of 10,11-dihydro-5H-dibenzo[a,d]cyclohepten-5-one (9.4 g, 45 mmol) and hydroxylamine hydrochloride (6.3 g, 90 mmol) pyridine (60 ml) was heated at reflux temperature for 48 h. Another portion of hydroxylamine hydrochloride (6.3 g, 90 mmol) was added and heating at reflux temperature was continued for another 24 h. The reaction mixture was allowed to cool and the solvent was evaporated in vacuo to give an oily residue, which was dissolved in a mixture of ethyl acetate (100 ml) and a 10% aqueous citric acid solution (100 ml). The phases were separated and the aqueous phase was extracted with ethyl acetate (50 ml). The combined organic phases were extracted with an aqueous citric acid solution (50 ml). The separated organic phase was washed with brine and dried over sodium sulphate. The solvent was evaporated in vacuo to a solid residue, which was recrystallized from cyclohexane. This afforded 5.4 g of the oxime derivative as a solid. TLC: rf=0.61 ($SiO_2$; dichloromethane/methanol=19:1).

To an ice-cooled mixture of the above oxime derivative (1.0 g, 4.5 mmol), tetrabutylammonium bromide (0.15 g, 0.5 mmol) and 1,2-dibromoethane (3.8 ml) was added a 12 M sodium hydroxide solution (5 ml). The reaction mixture was stirred vigorously for 4.5 h. A 2 M hydrochloric acid solution (50 ml) and diethyl ether (25 ml) was added. The phases were separated and the aqueous phase was extracted with diethyl ether (25 ml). The combined organic phases were washed with a 5% sodium bicarbonate solution, brine and dried over sodium sulphate. The solvent was evaporated in vacuo to give a residue, which was re-evaporated successively with ethanol, toluene, methanol and dichloromethane. This afforded 1.4 g of the crude 2-(((10,11-dihydro-5H-dibenzo[a,d]cyclohepten-5-ylidene)amino)oxy)ethylbromide as an oil. TLC: rf=0.65 ($SiO_2$; dichloromethane).

To a solution of 2-(((10,11-dihydro-5H-dibenzo[a,d]cyclohepten-5-ylidene)amino)oxy)ethylbromide (1.4 g, 4.2 mmol) in methyl isobutylketone (40 ml) was added potassium carbonate (4.7 g, 34 mmol) and ethyl (R)-3-piperidinecarboxylate tartrate (2.6 g, 8.5 mmol) and the suspension was heated at reflux temperature for 3 days. The cooled reaction mixture was filtered and the solvent was evaporated from the filtrate in vacuo. The oily residue was dissolved in a mixture of ethyl acetate (50 ml) and water (50 ml). A 34% aqueous tartaric acid solution was added until pH 4. The phases were separated and the aqueous phase was extracted with ethyl acetate (25 ml). The combined organic phases were extracted with a 34% aqueous tartaric acid solution (2×5 ml) and the organic extracts were discarded. The acidic aqueous phases were combined, diluted three times with water and ethyl acetate (40 ml) was added. A 4 N sodium hydroxide solution was added until pH 7 and the phases were separated. The organic phase was washed with brine and dried over sodium sulphate. The solvent was evaporated in vacuo to give 1 g of (R)-N-(2-(((10,11-dihydro-5H-dibenzo[a,d]cyclohepten-5-ylidene)amino)oxy)ethyl)-3-piperidinecarboxylic acid ethyl ester as an oil. TLC: rf=0.39 ($SiO_2$; dichloromethane/methanol/acetic acid=20:2:1).

The above ester (1.0 g, 3.0 mmol) was dissolved in ethanol (25 ml) and a 4 N sodium hydroxide solution (3.4 ml) was added. The mixture was stirred vigorously at room temperature for 22 h. The solvent was evaporated in vacuo to give an oily residue. Dichloromethane (75 ml) was added and the mixture was cooled on an ice-bath. A concentrated hydrochloric acid solution (1.6 ml) was added. The mixture was stirred vigorously for a few minutes and the phases were separated. The organic phase was dried over sodium sulphate and the solvent was evaporated in vacuo. The residue was re-evaporated three times with dichloromethane and once with acetone to give 0.95 g of the title compound as a foam.

M.P. 119° C.

$^1$H NMR (DMSO-d$_6$) δ4.5°–4.6 (m,2H).

EXAMPLE 8

(R)-N-(2-((10,11-Dihydro-5H-dibenzo[a,d]cyclohepten-5-ylidene)methoxy)ethyl)-3-piperidinecarboxylic acid hydrochloride To a solution of 10,11-dihydro-5H-dibenzo[a,d]cyclohepten-5-carboxaldehyde (11.3 g, 51 mmol, prepared in a similar way as described in Acta Chem. Scand. 1978, B33, 100–103) and tetrabutylammonium bromide (1.64 g, 5.1 mmol) in dichloromethane (100 ml) was added 1,2-dibromoethane (62 ml) and a 12 M sodium hydroxide solution (100 ml). The reaction mixture was stirred vigorously overnight and dichloromethane (100 ml) was added. The phases were separated and the aqueous phase was extracted with dichloromethane (100 ml). The combined organic phases were washed with a 0.2 M hydrochloric acid solution (100 ml), brine (25 ml) and dried over magnesium sulphate. The solvent was evaporated in vacuo to give 14.1 g of 2-((10, 11-dihydro-5H-dibenzo[a,d]cyclohepten-5-ylidene)methoxy)ethylbromide. TLC: rf=0.48 (SiO$_2$; ethyl acetate/n-heptane=1:4).

To a solution of 2-((10,11-dihydro-5H-dibenzo[a,d]cyclohepten-5-ylidene)methoxy)ethylbromide (14.0 g, 42.5 mmol) in acetone (100 ml) was added potassium carbonate (23.5 g, 170 mmol), potassium iodide (0.7 g) and ethyl (R)-3-piperidinecarboxylate tartrate (19.6 g, 64 mmol). The suspension was stirred at room temperature for 3 days. The reaction mixture was filtered and the solvent was evaporated from the filtrate in vacuo. The oily residue was dissolved in ethyl acetate (150 ml). A 34% aqueous tartaric acid solution (100 ml) was added and pH was adjusted to 2.5 with a 4 M aqueous sodium hydroxide solution. The phases were separated and the organic phase was washed with a 2.5% aqueous solution of sodium bicarbonate (100 ml) and a 5% aqueous sodium bicarbonate solution (25 ml). The combined aqueous phases were extracted with ethyl acetate (100 ml). The combined organic phases were dried over magnesium sulphate. The solvent was evaporated in vacuo to give 12.0 g of (R)-N-(2-((10,11-dihydro-5H-dibenzo [a, d]cyclohepten-5-ylidene)methoxy)ethyl)-3-piperidinecarboxylic acid ethyl ester as an oil. TLC: rf=0.45 (SiO$_2$; dichloromethane/methanol/acetic acid=20:2:1).

The above ester (2.0 g, 4.9 mmol) was dissolved in ethanol (20 ml) and a 4 N sodium hydroxide solution (4.9 ml) was added. The mixture was stirred at 50° C. for 2 h. Water (10 ml) was added and ethanol was evaporated in vacuo to give an aqueous residue. A 4 M aqueous hydrochloric acid solution (6.2 ml) was added followed by dichloromethane (50 ml). The phases were separated and the aqueous phase was extracted with dichloromethane (50 ml). The combined organic phases were washed with water (10 ml) and then dried over magnesium sulphate. The solvent was evaporated in vacuo and the residue dried in vacuo to give 1.71 g of the title compound as a solid.

M.P. 111°–114° C. (dec.). Calculated for C$_{24}$H$_{28}$ClNO$_3$½H$_2$O: C, 70.6%; H, 7.2%; N, 3.3%; Cl, 4.2%; Found: C, 70.2%; H, 7.0%; N, 3.2%; Cl, 4.5%.

EXAMPLE 9

N-(2-(2-(10,11-Dihydro-5H-dibenzo[a,d]cyclohepten-5-yl)ethoxy)ethyl)-1,2,5,6-tetrahydro-3-pyridinecarboxylic acid hydrochloride A solution of 5-(2-(2-hydroxyethoxy)ethylidene)-10,11-dihydro-5H-dibenzo[a,d]cycloheptene (2.4 g, 8.2 mmol, prepared as described in Example 3) in dioxane (25 ml) was hydrogenated at 10 atm. for 16 h at room temperature in the presence of 10% palladium on carbon catalyst (50% aqueous paste). The mixture was filtered and the solvent was evaporated in vacuo to give an oily residue, which was re-evaporated from carbontetrachloride. This afforded 2.2 g 2-(2-(10,11-dihydro-5H-dibenzo[a,d]cyclohepten-5-yl)ethoxy)ethanol as an oil.

A solution of the above alcohol (2.2 g, 7.4 mmol) in dry THF (20 ml) was placed under an atmosphere of nitrogen and placed on an ice-bath. A solution of n-butyllithium in hexanes (3.0 ml, 2.5 M) was added dropwise and the mixture was stirred for another 15 minutes. Methanesulfonyl chloride (0.85 g, 7.4 mmol) was added in one portion and the mixture was stirred on an ice-bath for 45 minutes. The solvent was evaporated in vacuo and the residue was dissolved in acetone (25 ml). Ethyl 1,2,5,6-tetrahydro-3-pyridinecarboxylate hydrochloride (1.5 g, 7.8 mmol) and potassium carbonate (2.5 g, 18 mmol) were added. The mixture was stirred at reflux temperature for 16 h. The mixture was filtered and the solvent was evaporated in vacuo. The oily residue was submitted to column chromatography on silica gel (150 g) using a mixture of ethyl acetate and n-heptane (1:1 ) as eluent. Collecting the proper fractions afforded 1.3 g of N-(2-(2-(10,11-dihydro-5H-dibenzo[a,d]cyclohepten-5-yl)ethoxy)ethyl)-1,2,5,6-tetrahydro-3-pyridinecarboxylic acid ethyl ester as an oil. TLC: rf=0.14 (SiO$_2$; ethyl acetate/n-heptane=1:1).

The above ester (1.3 g, 3.1 mmol) was dissolved in ethanol (10 ml) and a 4 N sodium hydroxide solution (2.3 ml) was added. The mixture was stirred at room temperature for 4 h. A 4 N hydrochloric acid solution was added until pH 1. Dichloromethane (400 ml) was added and the mixture was stirred vigorously for a few minutes and the phases were separated. The organic phase was dried over sodium sulphate and the solvent was evaporated in vacuo. The residue was re-evaporated with acetone, dissolved in acetone (50 ml) and left for crystallization. This afforded 0.45 g of the title compound as a solid.

M.P. 154°–155° C. Calculated for C$_{25}$H$_{30}$ClNO$_3$: C, 70.2%; H, 7.1%; N, 3.3%; Cl, 8.3%; Found: C, 70.1%; H, 7.2%; N, 3.1%; Cl, 8.2%.

EXAMPLE 10

(R)-N-(2-((3-(10,11-Dihydro-5H-dibenz[b,f]azepin-5-yl)-1-propyl)oxy)ethyl)-3-piperidinecarboxylic acid hydrochloride To a solution of 10,11-dihydro-5H-dibenz[b,f]azepine (8.1 g, 40 mmol) in dry dibutylether (60 ml) kept under an atmosphere of nitrogen, NaH (1.6 g, 40 mmol, 60% oil dispersion) was carefully added. The reaction mixture was heated at reflux temperature for 4 h and then allowed to cool to 80° C. 3-Bromo-1-propyl tetrahydro-2-pyranyl ether (10.7 g, 48 mmol) was added and the mixture was heated at reflux temperature for 16 h. To the cooled reaction mixture was added water (20 ml) and the phases were separated. From the organic phase the solvent was evaporated and the residue was dissolved in a mixture of MeOH (150 ml) and a 4 N aqueous HCl solution (50 ml). The mixture was heated at reflux temperature for 15 minutes and then stirred for 1 h at RT. Water (250 ml) was added and the mixture was extracted with ethyl acetate (2×200 ml). The combined organic extracts was dried (Na$_2$SO$_4$), filtered and the solvent evaporated in vacuo. This afforded a residue which was submitted to chromatography on silica gel (200 g) using a mixture of n-heptane and ethyl acetate (3:2) as eluent to give 5.5 g of 3-(10,11-dihydro-5H-dibenz[b,f]azepin-5-yl)-1-propanol as an oil. TLC: rf=0.30 (SiO$_2$; n-heptane/ethyl acetate=1:1).

A mixture of NaH (0.40 g, 10 mmol, 60% oil dispersion), 3-(10,11-dihydro-5H-dibenz[b,f]azepin-5-yl)-1-propanol (2.5 g, 10 mmol) and dry dibutylether (25 ml) was stirred for 16 h at reflux temperature under a nitrogen atmosphere. The reaction mixture was allowed to cool and 2-bromoethyl tetrahydro-2-pyranyl ether (2.5 g, 12 mmol) was added. Then the mixture was heated to reflux temperature and kept there for 16 h. To the cooled mixture was added water (10 ml) and the phases were separated. From the organic phase the solvent was evaporated in vacuo to give a residue which was submitted to chromatography on silica gel (200 g) using a mixture of n-heptane and ethyl acetate (7:3) as eluent. This afforded 1.5 g of the tetrahydro-2-pyranyl intermediate. TLC: rf=0.55 (SiO$_2$; n-heptane/ethyl acetate=1:1). This intermediate was dissolved in a mixture of methanol (30 ml) and a 4 N aqueous hydrochloric acid solution (15 ml) and the mixture was heated at reflux temperature for 15 minutes. The reaction mixture was allowed to cool and methanol was evaporated in vacuo. Water was added and the mixture was extracted with ethyl acetate. The organic extract was washed with a 5% aqueous sodium bicarbonate solution, dried over sodium sulphate and the solvent evaporated in vacuo. This afforded 0.6 g (20%) of 2-((3-(10,11-dihydro-5H-dibenz[b,f]azepin-5-yl)-1-propyl)oxy)ethanol as an oil. TLC: rf=0.33 (SiO$_2$; n-heptane/ethyl acetate=1:1).

A solution of the above alcohol (0.60 g, 2.0 mmol) in dry THF (15 ml) was placed under an atmosphere of nitrogen and then cooled on an ice-bath. A solution of n-butyllithium in hexanes (0.88 ml, 2.5 M) was added dropwise at 10° C. When addition was complete the mixture was stirred at 10° C. for 30 minutes. Methanesulfonyl chloride (0.25 g, 2.2 mmol) was added and the reaction mixture was stirred at room temperature for 90 minutes. The volatiles were evaporated in vacuo leaving a residue which was dissolved in acetone (20 ml). Ethyl (R)-3-piperidinecarboxylate (0.50 g, 3.0 mmol) and potassium carbonate (0.7 g, 5 mmol) were added and the suspension was stirred at room temperature for 16 h and the heated at reflux temperature for 7 h. The cooled reaction mixture was filtered and the solvent was evaporated in vacuo. The oily residue was submitted to column chromatography on silica gel (150 g) using a mixture of ethyl acetate and n-heptane (2:3) as eluent. Collecting the proper fractions afforded 0.4 g of (R)-N-(2((3-(10,11-dihydro-5H-dibenz[b,f]azepin-5-yl)-1-propyl)oxy)ethyl)-3-piperidinecarboxylic acid ethyl ester as an oil.

The above ester (0.4 g, 0.92 mmol) was dissolved in ethanol (10 ml) and a 4 N sodium hydroxide solution (0.70 ml) was added. The mixture was stirred at room temperature for 4 h. A 4 N hydrochloric acid solution was added until pH 1. Dichloromethane (300 ml) was added and the phases were separated. The organic phase was dried over sodium sulphate and the solvent was evaporated in vacuo. The residue was re-evaporated with acetone, dissolved in a mixture of ethyl acetate and acetone and left for crystallization. This afforded 0.13 g of the title compound as a solid.

M.P. 130°-132° C. Calculated for C$_{25}$H$_{33}$ClN$_2$O$_3$: C, 67.5%; H, 7.5%; N, 6.3%; Found: C, 67.3%; H, 7.7%; N, 6.1%.

EXAMPLE 11

E/Z-(R)-N-(2-((((10,11-Dihydro-5H-dibenzo[a,d]cyclohepten-5-yl)methylene)amino)oxy)ethyl)-3-piperidinecarboxylic acid hydrochloride A mixture of (10,11-dihydro-5H-dibenzo[a,d]cyclohepten-5-yl)carboxaldehyde (11.5 g, 52 mmol, prepared similarly as described Acta Chem. Scand. 1979, 33, 100) and hydroxylamine hydrochloride (7.2 g, 103 mmol) in 96% ethanol (50 ml) was stirred at room temperature for 2 days. A 10% aqueous citric acid solution (100 ml) was added together with ethyl acetate (100 ml). The phases were separated and the organic phase was washed successively with a 10% aqueous citric acid solution (50 ml), an excess of a saturated sodium bicarbonate solution and brine. The organic phase was dried over magnesium sulphate and the solvent was evaporated in vacuo to give a solid residue which was recrystallized from cyclohexane. This afforded 5.2 g of (10,11-dihydro-5H-dibenzo[a,d]cyclohepten-5-yl)carboxaldehydoxime as a solid.

To an ice-cooled mixture of the above oxime derivative (5.4 g, 23 mmol), tetrabutylammonium bromide (0.73 g, 2.3 mmol) and 1,2-dibromoethane (19.6 ml) was added a 12 M sodium hydroxide solution (30 ml). The reaction mixture was stirred vigorously for 1.5 h. The phases were separated and the aqueous phase was extracted with a small portion of toluene. The combined organic phases were diluted with another portion of toluene (50 ml) and washed successively with an aqueous citric acid solution (pH 6), an excess of a saturated sodium bicarbonate solution and brine. The organic phase was dried over magnesium sulphate and the solvent was evaporated in vacuo to give an oily residue which was re-evaporated successively with methanol and dichloromethane. This afforded 7.8 g of the crude 2-((((10,11-dihydro-5H-dibenzo[a,d]cyclohepten-5-yl)methylene)amino)oxy)ethylbromide as an oil. TLC: rf=0.62 (SiO$_2$; dichloromethane).

To a solution of the above crude bromide (7.0 g, 20 mmol) in acetone (100 ml) was added potassium carbonate (16.8 g, 122 mmol) and ethyl (R)-3-piperidinecarboxylate tartrate (12.5 g, 41 mmol) and the suspension was stirred at room temperature for 2.5 days. The solvent was evaporated in vacuo and the residue was dissolved in a mixture of ethyl acetate (100 ml) and water (100 ml). The phases were separated and the aqueous phase was extracted with ethyl acetate (50 ml). Water (100 ml) was added to the combined organic extracts and pH was adjusted to 4 with a 34% aqueous tartaric acid solution. The phases were separated and the organic phase was extracted with a 34% aqueous tartaric acid solution (3×18 ml). The three combined aqueous tartaric extracts were diluted with icewater (250 ml) and ethyl acetate was added (150 ml). A 4 N aqueous sodium hydroxide solution was added until pH 7 and the phases were separated. The organic phase was washed with a saturated sodium bicarbonate solution and brine. After drying over magnesium sulphate the solvent was evaporated in vacuo to give 6 g of (R)-N-(2-((((10,11-dihydro-5H-dibenzo[a,d]cyclohepten-5-yl)methylene)amino)oxy)ethyl)-3-piperidinecarboxylic acid ethyl ester as an oil. TLC: rf=0.20 (SiO$_2$; ethyl acetate/n-heptane=1:1).

The above ester (5.0 g, 12 mmol) was dissolved in ethanol (100 ml) and a 2 N aqueous sodium hydroxide solution (27 ml) was added. The mixture was stirred at room temperature for 16 h. The solvent was evaporated in vacuo to give an oily residue. Dichloromethane (160 ml) was added and the mixture was cooled on an ice-bath. A concentrated hydrochloric acid solution (5.5 ml) was added. The mixture was stirred vigorously for a few minutes and the phases were separated. The organic phase was dried over magnesium sulphate and the solvent was evaporated in vacuo to give 4.1 g of the title compound as a foam. The material isolated consists of an approx. 1:5 mixture of the E/Z isomers.

M.P. 110° C.

$^1$H NMR (DMSO-d$_6$) δMajor isomer: 5.03 (d, 1H), 7.94 (d, 1H);

Minor isomer: 5.49 (d, 1H), 7.57 (d, 1H).

EXAMPLE 12

(R)-N-(2-(2-(5,6,7,12-Tetrahydrodibenz[b,g]azocin-12-yl)ethoxy)ethyl)-3-piperidinecarboxylic acid hydrochloride To a solution of 5,6,7,12-tetrahydrodibenz[b,g]azocine (2.5 g, 12 mmol, prepared in a similar way as described in Chem. Pharm. Bull. 1978, 26, 942–950) and 2-(2-((tetrahydro-2-pyranyl)oxy)ethoxy)ethylchloride (3.0 g, 14 mmol) in toluene (50 ml) was added a suspension of sodium amide (1.50 g, 19 mmol, 50% wt suspension in toluene). The reaction mixture was heated at reflux temperature for 10 h. The mixture was allowed to cool to room temperature and water (52.5 ml) was carefully added. The phases were separated and the aqueous phase was extracted with toluene (50 ml). The combined organic phases were washed with water (2×5 ml), brine (15 ml) and dried over magnesium sulphate. The solvent was evaporated in vacuo. The oily residue was submitted to column chromatography on silica gel (150 g) using a mixture of ethyl acetate and n-heptane (1:4) as eluent. Collecting the proper fractions afforded 3.0 g of crude 12-(2-(2-((tetrahydro-2-pyranyl)oxy)ethoxy)ethyl)-5,6,7,12-tetrahydrodibenz[b,g]azocine. TLC: rf=0.11 (SiO$_2$; ethyl acetate/n-heptane=1:4).

To a solution of 12-(2-(2-((tetrahydro-2-pyranyl)oxy)ethoxy)ethyl)-5,6,7,12-tetrahydrodibenz[b,g]azocine (3.0 g, 7.8 mmol) in (30 ml) was added a 4 M aqueous sulfuric acid solution. The mixture was stirred at room temperature for 18 h. The reaction mixture was poured into a mixture of water (150 ml) and a 4 M aqueous sodium hydroxide solution (6.5 ml). Ethyl acetate (100 ml) was added and pH was adjusted to 8.5 with a 5% aqueous sodium bicarbonate solution. The phases were separated and the aqueous phase was extracted with ethyl acetate (50 ml). The combined organic phases were washed with brine (20 ml) and dried over magnesium sulphate. The solvent was evaporated in vacuo and the residue was re-evaporated with dichloromethane. This afforded 2.1 g of crude 2-(2-(5,6,7,12-tetrahydrodibenz[b,g]azocin-12-yl)ethoxy)ethanol. TLC: rf=0.39 (SiO$_2$; dichloromethane/methanol=19:1).

A mixture of the above alcohol (1.8 g, 6 mmol), triethylamine (2.5 ml) and toluene (30 ml) placed under an atmosphere of nitrogen was cooled on an ice-bath. A solution of methanesulfonyl chloride (1.7 g, 12 mmol) in toluene (5 ml) was added dropwise. Stirring was continued for 45 minutes on an ice-bath and then the temperature was allowed to reach ambient temperature. Water (20 ml) was added and the mixture was stirred at room temperature for 15 minutes. The phases were separated and the aqueous phase was extracted with toluene (20 ml). The combined organic phases were washed with a 5% aqueous sodium bicarbonate solution and dried over magnesium sulphate. The solvent was evaporated in vacuo to give an oil which was dissolved in toluene (30 ml). To this solution was added potassium carbonate (2.9 g, 21 mmol) and ethyl (R)-3-piperidinecarboxylate tartrate (3.7 g, 12 mmol). The suspension was heated at 100° C. for 24 h and then allowed to cool to ambient temperature. The mixture was filtered and the solid washed with toluene (20 ml). The solvent was evaporated in vacuo to give an oily residue which was submitted to column chromatography on silica gel (150 g) using a gradient of a mixture of ethyl acetate and n-heptane (1:4–1:1). Collecting the proper fractions afforded 1.27 g of (R)-N-(2-(2-(5,6,7,12-tetrahydrodibenz[b,g]azocin-12-yl)-ethoxy)ethyl)-3-piperidinecarboxylic acid ethyl ester as an oil. TLC: rf=0.39 (SiO$_2$; dichloromethane/methanol/acetic acid=20:2:1).

The above ester (1.2 g, 2.7 mmol) was dissolved in ethanol (5 ml). A 4 N aqueous sodium hydroxide solution (2 ml) and water (3 ml) were added. The mixture was heated at 50° C. with stirring for 1 h. Water (25 ml) was added and ethanol was evaporated in vacuo. The aqueous residue was extracted with diethyl ether (2×25 ml) which was discarded. Then a 4 N aqueous hydrochloric acid solution (3 ml) was added to the aqueous phase and the resulting acidic solution was extracted with dichloromethane (2×50 ml). From the combined dichloromethane extracts the solvent was evaporated in vacuo and the residue re-evaporated with acetone. The foamy residue was triturated with diethylether to give 0.71 g of an amorphous solid which was recrystallized from 2-propanol (35 ml). After drying in vacuo 0.45 g of the title compound was obtained as a white solid.

M.P. 203.5°–205.5° C. Calculated for C$_{25}$H$_{33}$ClN$_2$O$_3$: C, 67.5%; H, 7.5%; N, 6.3%; Cl, 8.0% Found: C, 67.5%; H, 7.7%; N, 6.0%; Cl, 7.9%.

EXAMPLE 13

(R)-N-(2-(2-(6,11-Dihydro-5H-dibenz[b,e]azepin-5-yl)ethoxy)ethyl)-3-piperidinecarboxylic acid formate To a solution of 6,11-dihydro-5H-dibenz[b,e]azepine (5.0 g, 26 mmol, Coll. Czechoslov. Chem. Commun. 1958, 23, 1330) and 2-(2-((tetrahydro-2-pyranyl)oxy)ethoxy)ethylchloride (6.4 g, 30 mmol) in toluene (25 ml) placed under an atmosphere of nitrogen was added a suspension of sodium amide (5.0 g, 64 mmol, 50% wt suspension in toluene). The reaction mixture was heated at reflux temperature for 8 h. The mixture was allowed to cool to room temperature and toluene (50 ml) was added. The phases were separated and the organic phase was washed with a 1 N aqueous hydrochloric acid solution (2×100 ml), excess of a 5 % aqueous sodium bicarbonate solution and brine (25 ml). After drying over magnesium sulphate the solvent was evaporated in vacuo. The oily residue was submitted to column chromatography on silica gel (250 g) using a mixture of ethyl acetate and n-heptane (1:4) as eluent. Collecting the proper fractions afforded 2.6 g of 12-(2-(2-((tetrahydro-2-pyranyl)oxy)ethoxy)ethyl)-6,11-dihydro-5H-dibenz[b,e]azepine. TLC: rf=0.41 (SiO$_2$; ethyl acetate/n-heptane=1:1).

To a solution of 12-(2-(2-((tetrahydro-2-pyranyl)oxy)ethoxy)ethyl)-6,11-dihydro-5H-dibenz[b,e]azepine (2.9 g, 7.9 mmol) in 2-propanol (30 ml) was added a 4 M aqueous sulfuric acid solution (6 ml). The mixture was stirred at room temperature for 1 h. The reaction mixture was poured into a mixture of water (100 ml) and toluene (25 ml). The phases were separated and the organic phase was washed with excess of a saturated aqueous sodium bicarbonate solution. The acidic aqueous phase was made alkaline with aqueous sodium hydroxide and extracted with toluene. The combined organic phases were washed with brine and dried over magnesium sulphate. The solvent was evaporated in vacuo to give 2.2 g of crude 2-(2-(6,11-dihydro-5H-dibenz[b,e]azepin-5-yl)ethoxy)ethanol. TLC: rf=0.17 (SiO$_2$; ethyl acetate/n-heptane=1:1).

A mixture of the above alcohol (2.1 g, 7.4 mmol), triethylamine (2.6 ml) and toluene (30 ml) placed under an atmosphere of nitrogen was cooled on an ice-bath. A solution of methanesulfonyl chloride (2.1 g, 15 mmol) in toluene (5 ml) was added dropwise. Stirring was continued for 45 minutes on an ice-bath and then the temperature was allowed to reach ambient temperature. Water (20 ml) was added and the mixture was stirred at room temperature for 15 minutes. The phases were separated and the organic phases were washed with a 5% aqueous sodium bicarbonate solution and brine and dried over magnesium sulphate. The solvent was evaporated in vacuo to give an oil which was dissolved in methyl isobutylketone (40 ml). To this solution was added potassium carbonate (3.6 g, 26 mmol) and ethyl (R)-3-piperidinecarboxylate tartrate (4.6 g, 15 mmol). The suspension was heated at 40° C. for 24 h and then at reflux temperature for 3 h. The reaction mixture was allowed to cool to ambient temperature and water (50 ml) was added. The phases were separated and from the organic phase the solvent was evaporated in vacuo. This afforded an oily residue which was submitted to column chromatography on silica gel (125 g) using a mixture of ethyl acetate and n-heptane (1:1) as eluent. Collecting the proper fractions afforded 1.0 g of (R)-N-(2-(2-(6,11-dihydro-5H-dibenz[b,e]azepin-5-yl)ethoxy)ethyl)-3-piperidinecarboxylic acid ethyl ester as an oil. TLC: rf=0.36 (SiO$_2$; ethyl acetate).

The above ester (1.0 g, 2.4 mmol) was dissolved in ethanol (25 ml) and a 2 N aqueous sodium hydroxide solution (4.7 ml) was added. The mixture was heated at 50° C. with stirring for 2.5 h. The volatiles were evaporated in vacuo and dichloromethane (100 ml) was added to the residue. The mixture was cooled on an ice-bath and a concentrated aqueous hydrochloric acid solution (1.2 ml) was added dropwise with vigorous stirring. The phases were separated and the organic phase was dried over magnesium sulphate. The solvent was evaporated in vacuo and the residue re-evaporated several times with acetone.

The residue was purified by column chromatography on silica gel using a mixture of dichloromethane, acetonitrile and formic acid (4:4:1 ) as eluent. The proper fractions were collected and the solvent was evaporated in vacuo to give a residue which was re-evaporated successively with n-heptane, dioxane and dichloromethane. This afforded 0.4 g of the title compound as a waxy solid.

$^1$H NMR (DMSO-d$_6$) δ4.13 (m, 1H); 4.67 (m, 1H).

EXAMPLE 14

(R)-N-(2-(2-(5,6,11,12-Tetrahydrodibenz[b,f]azocin-12-yl)ethoxy)ethyl)-3-piperidinecarboxylic acid hydrochloride To a solution of 2-(2-chloroethoxy)ethanol (3.9 g, 31 mmol) in dichloromethane (15 ml) kept at 0° C. was added triethylamine (6.2 g, 61 mmol). A solution of methanesulfonyl chloride (3.6 g, 31 mmol) in dichloromethane (15 ml) was carefully added keeping the temperature below 0° C. When addition was complete the reaction mixture was left overnight at room temperature and then diluted with dichloromethane (150 ml). The organic phase was washed with a 2 N hydrochloric acid solution (75 ml) and water (75 ml) and dried over magnesium sulphate. The solvent was evaporated in vacuo to give 6.3 g of crude 2-(2-chloroethoxy)ethyl mesylate as an oil. A suspension of 5,6,11,12-tetrahydrodibenz[b,f]azocine (5.0 g, 20 mmol) in dry THF (75 ml) placed under an atmosphere of nitrogen was cooled to −68° C. A solution of n-butyl lithium in hexanes (19 ml, 49 mmol, 2.5 M) was added dropwise keeping the temperature below −60° C. When addition was complete stirring was continued at this temperature for 30 minutes and then the reaction mixture was left overnight at room temperature. The mesylate prepared above was dissolved in dry THF (50 ml) and added dropwise to the reaction mixture. When addition was complete the mixture was stirred at room temperature for 168 h. Ice was added (80 g) and the phases were separated. The aqueous phase was extracted with diethyl ether (2×50 ml). The combined organic phases were washed with water (2×50 ml) and dried over magnesium sulphate. The solvent was evaporated in vacuo to give a residue which was submitted to column chromatography on silica gel using a mixture of ethyl acetate and n-heptane (2:3) as eluent. This afforded 2.5 g of 2-(2-(5,6,11,12-tetrahydrodibenz[b,f]azocin-12-yl)ethoxy)ethylchloride as an oil.

A mixture of the above chloride (2.5 g, 7.9 mmol), ethyl (R)-3-piperidinecarboxylate tartrate (2.4 g, 16 mmol) and potassium carbonate (3.3 g, 24 mmol) in methylisobutyl ketone (60 ml) was heated at reflux temperature for 96 h. The mixture was allowed to cool and the solvent was evaporated in vacuo. The residue was dissolved in a mixture of ethyl acetate (75 ml) and water (75 ml). The phases were separated and from the organic phase the solvent was evaporated in vacuo. The oily residue was submitted to column chromatography on silica gel using dichloromethane containing 5% of a mixture of ethanol and 25% aqueous ammonia (9:1) as eluent. The proper fractions were collected and the solvent was evaporated in vacuo. The residue was submitted once more to column chromatography on silica gel using dichloromethane containing 3% of a mixture of ethanol and 25% aqueous ammonia (9: 1) as eluent. The proper fractions were collected and the solvent was evaporated in vacuo to give 0.85 g of (R)-N-(2-(2-(5,6,11,12-tetrahydrodibenz[b,f]azocin-12-yl)ethoxy)ethyl)-3-piperidinecarboxylic acid ethyl ester as an oil.

The above ester (0.4 g, 0.9 mmol) was dissolved in ethanol (7 ml) and a 2 N aqueous sodium hydroxide solution (1.8 ml) was added. The reaction mixture was stirred at room temperature for 16 h. The mixture was placed on an ice-bath and a concentrated aqueous hydrochloric acid solution (0.37 ml) was added. The volatiles were evaporated in vacuo, the residue suspended in dichloromethane and the solid removed by filtration. The solvent was evaporated from the filtrate in vacuo to give a residue which was re-evaporated with dichloromethane to give 0.30 g of the title compound as an amorphous solid.

M.P. 60°–80° C.

Calculated for $C_{25}H_{33}ClN_2O_3 \cdot \frac{1}{4}CH_2Cl_2$: C, 65.1%; H, 7.2%; N, 6.0%; Found: C, 65.2%; H, 7.1%; N, 6.0%.

EXAMPLE 15

N-(2-(2-(10,11-Dihydro-5H-dibenz[b,f]azepin-5-yl)ethoxy)ethyl)-1,2,5,6-tetrahydro-3-pyridinecarboxylic acid hydrochloride To a solution of 2-(2-chloroethoxy)ethanol (15.3 g, 123 mmol) in toluene (100 ml) kept at 5° C. was added triethylamine (50 g, 500 mmol). A solution of methanesulfonyl chloride (28 g, 245 mmol) in toluene (50 ml) was carefully added keeping the temperature around 5° C. When addition was complete the reaction mixture was stirred at 5° C. for 45 minutes and then 75 minutes at ambient temperature. Water (100 ml) was added and the mixture was stirred for 15 minutes. The phases were separated and the organic phase was washed with water, brine and dried over magnesium sulphate. The solvent was evaporated in vacuo to give crude 2-(2-chloroethoxy)ethyl mesylate as an oil.

A solution of 10,11-dihydro-5H-dibenz[b,f]azepine (24 g, 123 mmol) in dry THF (100 ml) placed under an atmosphere of nitrogen was cooled to −70° C. A solution of n-butyl lithium in hexanes (49.2 ml, 123 mmol, 2.5 M) was added dropwise keeping the temperature below −60° C. When addition was complete stirring was continued at −70° C. for 15 minutes and then the reaction mixture was allowed to reach ambient temperature. The mesylate prepared above was dissolved in dry THF (50 ml) and added dropwise to the reaction mixture. When addition was complete the mixture was stirred at room temperature for 64 h. Water (100 ml) was added and the phases were separated. The aqueous phase was extracted with diethyl ether (50 ml). The combined organic phases were washed with brine and dried over magnesium sulphate. The solvent was evaporated in vacuo to give an oily residue which was submitted to column chromatography on silica gel (300 g, Lichroprep. 40–63μ) using a mixture of dichloromethane and n-heptane (1:5) as eluent. This afforded 10.4 g of 2-(2-(10,11-dihydro-5H-dibenz[b,f]-azepin-5-yl)ethoxy)ethylchloride as an oil. TLC: rf=0.23 (SiO$_2$; dichloromethane/n-heptane=1:1).

A mixture of the above chloride (5.0 g, 16.6 mmol), ethyl 1,2,5,6-tetrahydro-3-pyridinecarboxylate hydrochloride (6.3 g, 33 mmol), potassium carbonate (8.0 g, 58 mmol) and potassium iodide (0.55 g) in methylisobutyl ketone (50 ml) was heated at reflux temperature for 48 h. The reaction mixture was allowed to cool and water (50 ml) was added. The phases were separated and from the organic phase the solvent was evaporated in vacuo to give an oily residue. This residue was dissolved in a mixture of ethyl acetate (50 ml) and water (50 ml) and pH was adjusted to 4 with a 4% aqueous tartaric acid solution. The phases were separated and the organic phase was extracted with a 34% aqueous tartaric acid solution (3×15 ml). The three aqueous tartaric extracts were combined and icewater (150 ml) and ethyl acetate (100 ml) was added. A 12 N aqueous sodium hydroxide solution was added until pH 4 and the phases were separated. The organic phase was washed with a 5% sodium bicarbonate solution and brine and dried over magnesium sulphate. The solvent was evaporated in vacuo to give 6.0 g of N-(2-(2-(10,11-dihydro-5H-dibenz[b,f]azepin-5-yl)ethoxy)ethyl)-1,2,5,6-tetrahydro-3-pyridinecarboxylic acid ethyl ester as an oil. TLC: rf=0.47 (SiO$_2$; dichloromethane/methanol/acetic acid=20:2:1).

The above ester (5.0 g, 12 mmol) was dissolved in ethanol (250 ml) and a 2 N aqueous sodium hydroxide solution (24 ml) was added. The mixture was stirred at room temperature for 16 h. The solvent was evaporated in vacuo to give an oily residue. Dichloromethane (200 ml) was added and the mixture was cooled on an ice-bath. A concentrated hydrochloric acid solution (5.9 ml) was added. The mixture was stirred vigorously for a few minutes and the phases were separated. The organic phase was dried over magnesium sulphate and the solvent was evaporated in vacuo to give an oily residue which was re-evaporated with acetone. This afforded 4.8 g of the title compound as a foam.

M.P. 103° C. Calculated for $C_{24}H_{29}ClN_2O_3 \cdot H_2O$: C, 64.5%; H, 7.0%; N, 6.3%; Found: C, 64.9%; H, 6.9%; N, 5.9%.

$^1$H NMR (DMSO-d$_6$) δ3.53 (t, 2H); 3.95 (t, 2H); 6.96 (brs, 1H).

EXAMPLE 16

N-(2-(2-(10,11-Dihydro-5H-dibenz[b,f]azepin-5-yl)ethoxy)ethyl)-3-pyrrolidineacetic acid hydrochloride A mixture of 2-(2-(10,11-dihydro-5H-dibenz[b,f]azepin-5-yl)ethoxy)ethylchloride (1.5 g, 4.9 mmol, prepared as described in Example 15), methyl 3-pyrrolidineacetate acetate (2.0 g, 9.8 mmol), potassium carbonate (2.4 g, 17 mmol) and potassium iodide (0.16 g) in methylisobutyl ketone (30 ml) was heated at reflux temperature for 48 h. The reaction mixture was allowed to cool and water (40 ml) was added. The phases were separated and from the organic phase the solvent was evaporated in vacuo to give an oily residue. This residue was dissolved in a mixture of ethyl acetate (25 ml) and water (25 ml) and pH was adjusted to 4 with a 34% aqueous tartaric acid solution. The phases were separated and the organic phase was discarded. Ethyl acetate (25 ml) was added to the aqueous phase and pH was adjusted to approx. 9 with a 2 M aqueous sodium hydroxide solution. The phases were separated and from the organic phase the solvent was evaporated in vacuo to give an oily residue which was submitted to column chromatography on silica gel (180 ml) using a mixture of THF and n-heptane (1:1) as eluent. Collecting the proper fraction afforded 1.0 g of N-(2-(2 -(10,11-dihydro-5H-dibenz[b,f]azepin-5-yl)ethoxy)ethyl)-3-pyrrolidineacetic acid methyl ester as an oil.

The above ester (1.0 g, 2.5 mmol) was dissolved in ethanol (25 ml) and a 2 N aqueous sodium hydroxide solution (4.9 ml) was added. The mixture was stirred at room temperature for 16 h. The solvent was evaporated in vacuo to give an oily residue. Dichloromethane (100 ml) was added and the mixture was cooled on an ice-bath. A concentrated hydrochloric acid solution (1 ml) was added dropwise. The mixture was stirred vigorously for 15 minutes at approx. 10° C. Magnesium sulphate was added and the mixture was stirred at ambient temperature for 30 minutes and filtered. The solvent was evaporated in vacuo to give 0.9 g of the title compound as a foam.

M.P. 138° C.

$^1$H NMR (DMSO-d$_6$) δ3.54 (t, 2H); 3.94 (t, 2H).

EXAMPLE 17

(R)-N-(2-(2-(3,7-Dichloro-10,11-dihydro-5H-dibenz[b,f]azepin-5-yl)ethoxy)ethyl)-3-piperidinecarboxylic acid hydrochloride To a solution of 3,7-dichloro-10,11-dihydro-5H-dibenz[b,f]azepine (2.0 g, 7.6 mmol, prepared as described in British Patent No. 777,546)) in dry dimethylsulfoxide (20 ml) placed under an atmosphere of nitrogen was added sodium hydride (0.36 g as a 55% oil dispersion, 8.3 mmol). The reaction mixture was stirred at 70° C. for 1 h and then allowed to cool to ambient temperature. 2-(2-((Tetrahydro-2-pyranyl)oxy)ethoxy)ethylchloride (1.7 g, 8.3 mmol) was added and the mixture was stirred at room temperature for two days. The reaction mixture was poured into icewater and extracted with ethyl acetate (2×200 ml). The combined organic extracts were washed with water and dried over magnesium sulphate. The solvent was evaporated in vacuo to give 3.7 g of an oil which was dissolved in methanol (100 ml). A 4 N aqueous hydrochloric acid solution (30 ml) was added and the mixture was stirred at 50° C. for 1 h. The cooled reaction mixture was diluted with water (700 ml) and extracted with ethyl acetate (2×200 ml). The combined organic extracts were washed with a saturated aqueous sodium bicarbonate solution and dried over magnesium sulphate. The solvent was evaporated in vacuo to give an oily residue which was submitted to column chromatography on silica gel (100 g) using a mixture of ethyl acetate and n-heptane (3:7) as eluent. Collecting the proper fractions afforded 1.3 g of 2-(2-(3,7-dichloro-10,11-dihydro-5H-dibenz[b,f]azepin-5-yl)ethoxy)ethanol as an oil. TLC: rf=0.32 (SiO$_2$; ethyl acetate/n-heptane=1:1).

To a mixture of the above alcohol (1.3 g, 3.7 mmol), triethylamine (1.3 ml) and dry diethyl ether (75 ml) was added dropwise a solution of methanesulfonyl chloride (0.63 g, 5.5 mmol) in dry diethyl ether (25 ml). Stirring was continued for 1 h at room temperature. The reaction mixture was washed with water and dried over potassium carbonate. The solvent was evaporated in vacuo to give an oily residue which was dissolved in acetone (30 ml). To this solution was added potassium carbonate (1.0 g, 7.4 mmol) and ethyl (R)-3-piperidinecarboxylate (1.2 g, 7.4 mmol) and the suspension was heated at reflux temperature for 16 h. Another portion of ethyl (R)-3-piperidinecarboxylate (0.5 g) was added and the mixture was heated at reflux temperature for 24 h. This cooled reaction mixture was filtered and from the filtrate the solvent was evaporated in vacuo. This afforded an oil which was submitted to column chromatography on silica gel (100 g) using a mixture of ethyl acetate and n-heptane (1:1) as eluent. Collecting the proper fractions gave 1.5 g of (R)-N-(2-(2-(3,7-dichloro-10,11-dihydro-5H-dibenz[b,f]-azepin-5-yl)ethoxy)ethyl)-3-piperidinecarboxylic acid ethyl ester as an oil. TLC: rf=0.18 (SiO$_2$; ethyl acetate/n-heptane=1:1).

The above ester (1.5 g, 3.1 mmol) was dissolved in ethanol (20 ml). A 4 N aqueous sodium hydroxide solution (2.3 ml) was added and the mixture was stirred at ambient temperature for 3 h. A concentrated aqueous hydrochloric acid solution (3 ml) was added until pH 1 and the mixture was extracted with dichloromethane (300 ml). The phases were separated and the organic phase was washed with water (10 ml) and dried over magnesium sulphate. The solvent was evaporated in vacuo and the residue re-evaporated with acetone. The foamy residue was dissolved in acetone (20 ml) and left for crystallization. This afforded 1.25 g of the title compound as a solid.

M.P. 212°–213° C. Calculated for C$_{24}$H$_{29}$Cl$_3$N$_2$O$_3$; C, 57.7%; H, 5.9%; N, 5.6%; Found: C, 57.7%; H, 6.1%; N, 5.2%.

EXAMPLE 18

(R)-N-(3-(2-(5H-Dibenzo[a,d]cyclohepten-5-ylidene)ethoxy)-1-propyl)-3-piperidinecarboxylic acid hydrochloride A mixture of 5-(ethylidene)-10,11-dihydro-5H-dibenzo[a,d]cycloheptene (4.0 g, 18 mmol, prepared similar as described in J. Med. Chem. 1990, 33, 3095), dibenzoyl peroxide (60 mg), N-bromosuccinimide (3.2 g, 18 mmol) and carbontetrachloride (20 ml) was heated at reflux temperature for 18 h. N-bromosuccinimide (1.6 g, 9 mmol) was added and the mixture was heated at reflux temperature for 24 h. The mixture was allowed to cool and then filtered through silica gel (50 ml) and the gel was washed with dichloromethane (150 ml). From the combined filtrate and washing the solvents were evaporated in vacuo to give 6.85 g of an oil. A solution of n-butyllithium (6.7 ml, 16.7 mmol, 2.5 M) was added dropwise to ice-cooled propylene glycol (100 ml) under an atmosphere of nitrogen. When addition was complete the mixture was stirred at room temperature for 90 minutes. A solution of the crude bromide prepared above (5 g) dissolved in toluene (50 ml) was added and the mixture was stirred at room temperature for 3 days. The mixture was diluted with water (100 ml) and the phases were separated. The aqueous phase was extracted with toluene (2×50 ml). The combined organic extracts were washed with water (50 ml), brine and dried over sodium sulphate. The solvent was evaporated in vacuo to give a residue which was submitted to column chromatography on silica gel (225 g) using a mixture of THF and n-heptane (3:7) as eluent. Collecting the proper fractions afforded 0.6 g of 3-(2-(5H-dibenzo[a,d]cyclohepten-5-ylidene)ethoxy)-1-propanol as an oil.

A mixture of the above alcohol (0.6 g, 2.0 mmol) and triethylamine (0.52 g, 5.1 mmol) in toluene (10 ml) was placed on an ice-bath under an atmosphere of nitrogen. A solution of methanesulfonyl chloride (0.59 g, 4.1 mmol) in toluene (1.5 ml) was added keeping the temperature below 10° C. When addition was complete the mixture was stirred for 45 minutes at 5° C. and 30 minutes below 15° C. Water was added (5 ml) and the mixture was stirred at ambient temperature for 15 minutes. The phases were separated and the aqueous phase was extracted with toluene (5 ml). The combined organic phases were washed with a 5% aqueous sodium bicarbonate solution, brine and dried over sodium sulphate. The solvent was evaporated in vacuo to give a residue which was dissolved in toluene (10 ml). Ethyl (R)-3-piperidinecarboxylate tartrate (1.25 g, 4.1 mmol) and potassium carbonate (0.98 g, 7.1 mmol) was added and the mixture was heated at reflux temperature for 16 h. The mixture was allowed to cool and then filtered. The solvent was evaporated from the filtrate leaving an oil which was dissolved in ethyl acetate (20 ml). Water (20 ml) was added and pH was adjusted to 4 with a 34% aqueous tartaric acid solution. The phases were separated and the aqueous phase was extracted with ethyl acetate (10 ml). The organic phases were combined and washed with excess of a 5% aqueous sodium bicarbonate solution, brine and dried over sodium sulphate. The solvent was evaporated in vacuo to give an oil which was re-evaporated successively with methanol and dichloromethane. This afforded 0.77 g of an oil which was dissolved in toluene (15 ml) and extracted with a 34% aqueous tartaric acid solution (15+7 ml). The combined aqueous extracts were washed with toluene (5 ml) and the toluene phases were discarded. The acidic aqueous phase was diluted with water (30 ml) and ethyl acetate (50 ml) was added. A 4 N aqueous sodium hydroxide solution (12 ml) and excess of a 5% aqueous sodium bicarbonate solution was added. The phases were separated and the aqueous phase was extracted with ethyl acetate (30 ml). The combined ethyl acetate extracts were washed with brine and dried over sodium sulphate. The solvent was evaporated in vacuo to give an oil which was re-evaporated successively with methanol and dichloromethane. This afforded 0.42 g of (R)-N-(3-(2-(5H-dibenzo[a,d]-cyclohepten-5-ylidene)ethoxy)-1-propyl)-3-piperidinecarboxylic acid ethyl ester as an oil.

The above ester (0.42 g, 1.0 mmol) was dissolved in ethanol (5 ml) and a 12 N aqueous sodium hydroxide solution (0.36 ml) was added. The mixture was stirred at room temperature for 3.5 h and the solvent was evaporated in vacuo to give an oily residue. Dichloromethane (30 ml) was added and the mixture was cooled on an ice-bath. A concentrated hydrochloric acid solution (0.45 ml) was added dropwise and a small amount of icewater was added to dissolve the solid formed. The phases were separated and the organic phase was dried over sodium sulphate. The solvent was evaporated in vacuo to give an oily residue which was re-evaporated with dichloromethane. This afforded 0.43 g of the title compound as an amorphous solid.

M.P. 114°–119° C.

$^1$H NMR (DMSO-d6) δ3.77 (dd, 1H); 4.08 (dd, 1H); 5.63 (dd, 1H); 6.90–6.97 (m, 2H).

We claim:

1. A compound of formula I

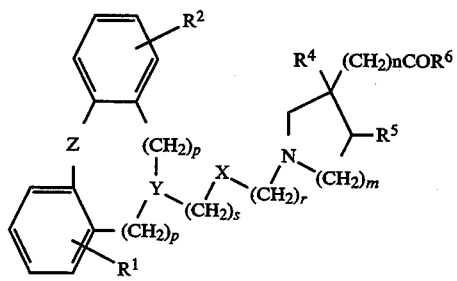

wherein $R^1$ and $R^2$ independently are hydrogen, halogen, trifluoromethyl, $C_{1-6}$-alkyl or $C_{1-6}$-alkoxy;

Y is >CH—$CH_2$— or >C=CH— when s is 0, 1 or 2 or Y is >CH—CH=NH— or >C=N— when s is 0, wherein the underscored atom is part of the ring system;

X is —O—;

Z is —$CH_2$—, —$CH_2$—$CH_2$—, CH=CH—$CH_2$—, —$CH_2$—CH=CH—, —$CH_2$—$CH_2$—$CH_2$— or —CH=CH—;

$R^4$ and $R^5$ independently are hydrogen or together represent a bond;

$R^6$ is OH or $C_{1-8}$-alkoxy;

p is 0 or 1;

q is 0 or 1;

s is 0, 1 or 2;

r is 2, 3 or 4;

m is 2; and n is 0; or a pharmaceutically acceptable salt thereof.

2. A compound according to claim 1 wherein Z is —$CH_2$—$CH_2$—.

3. A compound according to claim 1, wherein s is 1.

4. A compound according to claim 1, wherein Y is >CH—CH=N— and s is 0.

5. A compound according to claim 1, wherein p and q are 0.

6. A compound according to claim 1, wherein r is 2.

7. A compound according to claim 1, wherein Z is —$CH_2$—$CH_2$—, p and q are 0 and r is 2.

8. A compound according to claim 7, wherein s is 1.

9. A compound according to claim 7 wherein Y is >CH—CH=N— and s is 1.

10. A compound according to claim 1 which is:

(R)-N-(2-(2-(10,11-Dihydro-5H-dibenzo[a,d]cyclohepten-5-ylidene)ethoxy)ethyl)-3-piperidinecarboxylic acid;

(R)-N-(2-(2-(10,11-Dihydro-5H-dibenzo[a,d]cyclohepten-5-yl)ethoxy)ethyl)-3-piperidinecarboxylic acid;

(R)-N-(3-(2-(10,11-Dihydro-5H-dibenzo[a,d]cyclohepten-5-ylidene)ethoxy)-1-propyl)-3-piperidinecarboxylic acid;

(R)-N-(3-(2-(10,11-Dihydro-5H-dibenzo[a,d]cyclohepten-5-yl)ethoxy)-1-propyl)-3-piperidinecarboxylic acid;

(R)-N-(2-(((10,11-Dihydro-5H-dibenzo[a,d]cyclohepten-5-ylidene)amino)oxy)ethyl)-3-piperidinecarboxylic acid;

(R)-N-(2-((10,11-Dihydro-5H-dibenzo[a,d]cyclohepten-5-ylidene)methoxy)ethyl)-3-piperidinecarboxylic acid;

(R)-N-(2-(2-(10,11-Dihydro-5H-dibenzo[a,d]cyclohepten-5-yl)ethoxy)ethyl)-1,2,5,6-tetrahydro-3-pyridinecarboxylic acid;

(R)-N-(2-((((10,11-Dihydro-5H-dibenzo[a,d]cyclohepten-5-yl)methylene)amino)oxy)ethyl)-3-piperidinecarboxylic acid;

(R)-N-(2-(3-(2-(5H-Dibenzo[a,d]cyclohepten-5-ylidene)ethoxy)-1-propyl)-3-piperidinecarboxylic acid; or a pharmaceutically acceptable salt thereof.

11. A pharmaceutical composition comprising a compound according to claim 1 together with a pharmaceutically acceptable carrier or diluent.

12. A pharmaceutical composition suitable for treating a central nervous system ailment related to the GABA uptake comprising an effective amount of a compound according to claim 1 together with a pharmaceutically acceptable carrier or diluent.

13. The pharmaceutical composition according to claim 11 comprising between 0.5 mg and 1000 mg of the compound per unit dose.

14. The pharmaceutical composition according to claim 12 comprising between 0.5 mg and 1000 mg of the compound per unit dose.

15. A method of treating a central nervous system ailment related to the GABA uptake in a subject in need thereof comprising administering to said subject an effective amount of a compound according to claim 1.

16. A method of treating a central nervous system ailment related to the GABA uptake in a subject in need thereof comprising administering to said subject a pharmaceutical composition according to claim 12.

* * * * *